(12) United States Patent
Banker

(10) Patent No.: US 10,478,637 B2
(45) Date of Patent: Nov. 19, 2019

(54) SYSTEM AND METHOD FOR LIMITING CHEMOTHERAPY-INDUCED ALOPECIA

(71) Applicant: William R. Banker, Cincinnati, OH (US)

(72) Inventor: William R. Banker, Cincinnati, OH (US)

(73) Assignee: Hair Science Systems LLC, Cincinnati, OH (US)

( * ) Notice: Subject to any disclaimer, the term of this patent is extended or adjusted under 35 U.S.C. 154(b) by 503 days.

(21) Appl. No.: 15/143,475

(22) Filed: Apr. 29, 2016

(65) Prior Publication Data

US 2016/0317348 A1 Nov. 3, 2016

Related U.S. Application Data

(60) Provisional application No. 62/154,818, filed on Apr. 30, 2015.

(51) Int. Cl.
*A61N 5/06* (2006.01)
*A61H 9/00* (2006.01)
(Continued)

(52) U.S. Cl.
CPC ............. *A61N 5/0617* (2013.01); *A61F 7/10* (2013.01); *A61H 9/0078* (2013.01); *A61F 2007/0002* (2013.01); *A61F 2007/0008* (2013.01); *A61F 2007/0056* (2013.01); *A61F 2007/0091* (2013.01); *A61F 2007/0096* (2013.01); *A61F 2007/0273* (2013.01); *A61F 2007/0287* (2013.01); *A61H 2201/0214* (2013.01); *A61H 2201/0242* (2013.01); *A61H 2201/10* (2013.01); *A61H 2205/021* (2013.01);
(Continued)

(58) Field of Classification Search
CPC ...... A61H 9/005; A61H 9/078; A61H 9/0092; A61H 2205/02–021; A61H 2201/02; A61H 2201/0214–0221; A61H 2201/0242; A61H 2201/0264; A61H 2201/0278–0285; A61N 5/0617; A61N 7/02; A61N 2007/0002; A61N 2007/0091; A61N 2007/0092; A61N 2007/0096; A61N 2007/0225–0233; A61N 2007/0241; A61N 2007/0244; A61N 2007/0273; A61N 2007/0287; A61N 2007/10
See application file for complete search history.

(56) References Cited

U.S. PATENT DOCUMENTS 4,149,541 A 4/1979 Gammons et al.
4,844,072 A 7/1989 French et al.
(Continued)

FOREIGN PATENT DOCUMENTS

CA 2300877 A1 2/1999
GB 2107193 A 4/1983
(Continued)

*Primary Examiner* — Rachel T Sippel
(74) *Attorney, Agent, or Firm* — Porter Wright Morris & Arthur LLP

(57) ABSTRACT

A cold cap adapted for connecting to a chiller unit for circulating chilled fluid through the cap. The cap is formed from at least three layers of material which are sealingly attached around their periphery so as to form a cooling fluid chamber, wherein the cap is configured to apply compression and cooling to the scalp.

2 Claims, 9 Drawing Sheets

(51) Int. Cl.
  *A61F 7/10*    (2006.01)
  *A61F 7/00*    (2006.01)
  *A61F 7/02*    (2006.01)
  *A61N 5/067*   (2006.01)

(52) U.S. Cl.
  CPC .............. *A61N 2005/067* (2013.01); *A61N 2005/0652* (2013.01); *A61N 2005/0662* (2013.01)

(56) References Cited

U.S. PATENT DOCUMENTS

| | | | |
|---|---|---|---|
| 5,603,728 A | 2/1997 | Pachys | |
| 5,871,526 A * | 2/1999 | Gibbs | A61F 7/02 165/46 |
| 5,897,581 A * | 4/1999 | Fronda | A61F 7/10 607/109 |
| 6,156,059 A | 12/2000 | Olofsson | |
| 6,178,562 B1 * | 1/2001 | Elkins | A41D 13/005 2/102 |
| 6,312,453 B1 * | 11/2001 | Stefanile | A61F 7/10 607/108 |
| 7,405,080 B2 | 7/2008 | Voellmy | |
| 7,640,764 B2 | 1/2010 | Gammons et al. | |
| 7,722,655 B2 | 5/2010 | Lee | |
| 9,132,057 B2 * | 9/2015 | Wilford | A61H 9/0092 |
| 2007/0068651 A1 | 3/2007 | Gammons et al. | |
| 2009/0069731 A1 | 3/2009 | Parish et al. | |
| 2010/0106229 A1 | 4/2010 | Gammons et al. | |
| 2010/0168825 A1 * | 7/2010 | Barbknecht | A61F 7/103 607/110 |
| 2010/0186436 A1 * | 7/2010 | Stormby | A61F 7/10 62/259.3 |
| 2011/0098610 A1 | 4/2011 | Gammons | |
| 2012/0041526 A1 | 2/2012 | Stormby | |
| 2012/0130457 A1 * | 5/2012 | Gammons | A61F 7/02 607/104 |
| 2013/0030331 A1 | 1/2013 | Quisenberry et al. | |
| 2013/0138185 A1 | 5/2013 | Paxman et al. | |
| 2014/0046410 A1 | 2/2014 | Wyatt | |
| 2018/0055721 A1 | 3/2018 | Quisenberry et al. | |

FOREIGN PATENT DOCUMENTS

| | | |
|---|---|---|
| GB | 2323915 B | 4/2001 |
| GB | 2482792 B | 2/2012 |
| WO | 8204184 A1 | 12/1982 |
| WO | 9816176 A1 | 4/1998 |
| WO | 03047479 A1 | 6/2003 |

* cited by examiner

SYSTEM AND METHOD FOR LIMITING CHEMOTHERAPY-INDUCED ALOPECIA

CROSS REFERENCE TO RELATED APPLICATIONS

This application claims priority to U.S. Provisional Patent Application Nos. 62/154,818 filed on Apr. 30, 2015, entitled "SYSTEM AND METHOD FOR LIMITING CHEMOTHERAPY-INDUCED ALOPECIA." The entire disclosure of the foregoing provisional patent application is incorporated by reference herein.

BACKGROUND

Chemotherapy frequently induces hair loss (also referred to as alopecia). With chemotherapy, patients not only experience reduced stamina and independence but also must wear a physical symbol of their illness in the loss of their hair. This loss of hair is a traumatic experience that may well result in lower self-esteem and overall resistance. In fact, some patients are known to have refused chemotherapy for fear of losing their hair.

Scalp tourniquets have been used for several decades in an attempt to prevent chemotherapy-induced alopecia. This technique involves the placement of a pneumatic tourniquet around the hairline at the time of administration of the chemotherapeutic drug. The tourniquet is then inflated to a pressure above the systolic arterial pressure, in order to reduce blood flow to the scalp. The effectiveness of this technique has never been unambiguously demonstrated.

The use of scalp tourniquets has more or less been replaced by scalp hypothermia. With this technique, the scalp temperature is lowered to below 24° C. by application of cold packs, etc., prior to chemotherapy. Hypothermy has been reported to afford a 50-70% good to excellent hair protective effect. However, results have remained notoriously variable. Furthermore, hair thinning is still unsatisfactory for an unacceptably large number of patients, resulting in a preference to wear a wig in public rather than display thinning hair. By way of example, U.S. Pat. No. 5,603,728 (herein incorporated by reference) describes an attempt to minimize alopecia using hypothermy by use of a fluid circulating cap. While such scalp cooling reduces the cytotoxic effect chemotherapy drugs on hair follicles, follicles are still damaged.

Pharmacologic approaches to preventing chemotherapy-induced alopecia have also been used. For example, U.S. Pat. No. 7,405,080 (herein incorporated by reference) discloses that several pharmacological approaches for the prevention of chemotherapy-induced hair loss have been tested. But currently applicant is not aware of any drug on the market that generally protects against chemotherapy-induced alopecia, and there are only few drug candidates believed to be under active development.

Photo-stimulation of follicles has been attempted for the amelioration of alopecia, such as described in U.S. Pat. No. 7,722,655 (herein incorporated by reference). Photo-stimulation is used to stimulate regrowth of hair follicles, particularly after hair thinning is detected, and has been used with some success.

Furthermore, all of the previous methods have unwanted side effects from either the cooling process or chemicals.

While a variety of devices and techniques have been proposed for ameliorating the effects of chemotherapy-induced alopecia, it is believed that no one prior to the inventor has made or used an invention as described herein.

BRIEF DESCRIPTION OF THE DRAWINGS

It is believed the present invention will be better understood from the following description of certain examples taken in conjunction with the accompanying drawings. In the drawings, like numerals represent like elements throughout the several views.

Figure 1:
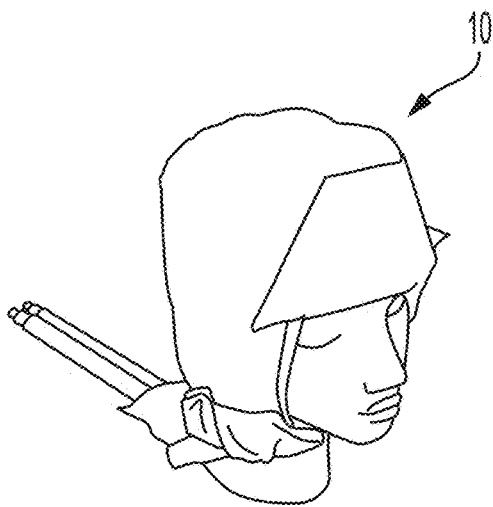
FIG. 1 depicts one embodiment of a cold cap assembly shown fully fitted on a head.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples should not be used to limit the scope of the present invention. Other features, aspects, and advantages of the versions disclosed herein will become apparent to those skilled in the art from the following description, which is by way of illustration, one of the best modes contemplated for carrying out the invention. As will be realized, the versions described herein are capable of other different and obvious aspects, all without departing from the invention. Accordingly, the drawings and descriptions should be regarded as illustrative in nature and not restrictive.

The present invention relates to systems and methods for preventing or limiting chemotherapy-induced alopecia. Methods to enhance hair retention, ameliorate symptoms of alopecia, and improve the success of treatment are also provided. In some embodiments, scalp cooling is used to reduce the exposure of hair follicles to alopecia-inducing products of chemotherapy, with or without scalp compression. In additional embodiments, scalp cooling (with or without compression) is used in combination with follicle stimulation to promote hair regrowth. For example, scalp cooling is used in conjunction with (i.e., prior to) photo-stimulation of the scalp such as low-level laser therapy.

While it is generally known that photo-stimulation can stimulate hair regrowth in people who experience hair thinning, the cytotoxic effects of chemotherapy usually injure hair follicles to such a degree that there are little or no follicles left in a state to stimulate to grow following chemotherapy. In addition, since photo-stimulation results in increased blood flow to the scalp, it can actually result in increased hair loss when used in conjunction with chemotherapy. However, applicant has surprisingly found that by combining scalp cooling and photo-stimulation in a treatment regime, chemotherapy-induced hair loss is reduced far more than expected.

Scalp cooling in combination with scalp compression is also provided by some embodiments of the system and method described herein, in order to reduce chemotherapy-induced hair loss more than when scalp cooling alone is used. In some embodiments, scalp cooling is commenced prior to the administration of chemotherapeutic agent(s) to the patient such that the scalp is sufficiently cooled when administration of the agent(s) begins. Scalp compression, when employed, is also commenced prior to administration of the chemotherapeutic agent(s) in order to not only enhance scalp cooling but also to reduce blood flow to the scalp. In some embodiments, scalp compression is stopped at or about the time that administration of the chemotherapeutic agent(s) is completed, while scalp cooling is continued (as further described below).

In one example treatment regime, scalp cooling is begun prior to administration of chemotherapeutic agent(s) (e.g., about 30 minutes prior), and scalp temperature is gradually lowered over this pre-chemo ("pre-treatment") time period. Scalp compression may also commence at the same time as scalp cooling, sometime thereafter (e.g., prior to infusion of chemo. agent(s)), or at the time administration of the chemo. agent(s) commences. In some treatment regimes, it may be desirable to begin scalp compression after scalp cooling begins (e.g., about 15 minutes after cooling begins and about 15 minutes prior to infusion) for purposes of patient comfort. Since scalp compression affects cooling (i.e., compression increases the rate of scalp cooling), it may be desirable to delay compression and/or gradually increase the amount of pressure applied to the scalp so that the scalp does not cool too rapidly for patient comfort and/or safety.

Scalp cooling, as well as scalp compression when employed, is continued (i.e., scalp temperature maintained at the desired level) throughout administration (e.g., infusion) of the chemotherapeutic agent(s) and for a period of time afterwards (e.g., for about 120 to 180 minutes after administration of the chemotherapeutic agent(s) has ended). While administration of chemotherapeutic agents is typically done by infusion (e.g., using an infusion pump), the systems and methods described herein may also be used in conjunction with other forms of administration such as chemotherapeutic agents delivered orally.

Since the chemotherapeutic agent(s) will continue to circulate in the bloodstream for a period of time after administration of the chemotherapeutic agent(s) has ended, post-treatment scalp cooling will continue to protect hair follicles. The period of post-treatment scalp cooling may be adjusted, as necessary, based on, for example, the half-life of the chemotherapeutic agent(s) administered to the patient as well as for purposes of patient comfort. The half-life of the chemotherapeutic agent(s) simply refers to the amount of time necessary for the agent(s) to lose one half of its pharmacologic/physiologic activity, and is dependent upon not only the specific agent(s) administrated to the patient, but also dosage as well as patient-specific factors (e.g., patient weight, liver function, etc.).

Following administration of chemotherapy and scalp cooling, in some embodiments photo-stimulation is administered to the patient's scalp. However, photo-stimulation generally should not be administered too soon, else the patient may lose more hair rather than retain more hair and/or regrow new hair. For example, photo-stimulation (e.g., low-level laser therapy) may be commenced after the chemotherapeutic agent(s) have lost at least 50%, or even 75% (or 90%) of its activity. Since the half-lives of chemotherapeutic agents are generally known to oncologists and other medical practitioners, the lag time between chemotherapy and photo-stimulation may be tailored to each patient based on their particular chemotherapy regime. Patients are often administered chemotherapy in "rounds" extending over several days, with the chemotherapeutic agent(s) administered at preset intervals over the duration of the round. In some embodiments of the treatment methods and protocols herein, photo-stimulation is not administered until after the round has been completed and the activity of the chemotherapeutic agent(s) has reduced to a desired level (e.g., at least a 50%, 75%, or 90% reduction in activity). The cooling unit and/or laser therapy systems described further herein may even be configured to not only commence and end scalp cooling (and optionally scalp compression) at the desired times (e.g., when the activity of the chemo. agent(s) has been reduced to at least 50%), but also inform a patient when it is appropriate to begin photo-stimulation (e.g., based on input provided to the unit or system by a medical practitioner or the patient).

In one exemplary embodiment, a cold cap is used in combination with a portable refrigeration unit for purposes of scalp cooling. Applicant has found that by separating the source of refrigeration from the scalp of the patient (e.g., by at least one meter), several benefits are observed, including making the treatment easier to manage. In addition, applicant has discovered that by controlling the rate of cooling of the scalp, the therapy is much better tolerated by the patient with less complaint of cold. This same finding can be applied to other regions of the body, with or without follicles, which benefit from localized cooling. The rate of scalp cooling may be controlled, for example, by regulating the temperature of cooled fluid delivered to the cold cap, regulating the flow rate of cooled fluid through the cap, and/or regulating the amount of scalp compression (i.e., the pressure of the fluid delivered to the cool cap for purposes of compression).

Chemotherapy is done in clinical and home settings. In clinical settings, patient space is often expensive, necessitating that patients leave once chemotherapy is complete. Since previous methods of scalp cooling required monitoring by a clinician to prevent injury, hypothermy was often terminated at the same time administration of the chemo. agent(s) was completed. The necessity for clinician monitoring of hypothermy furthermore eliminated its use when chemotherapy was administered at home by the patient.

Figure 2:
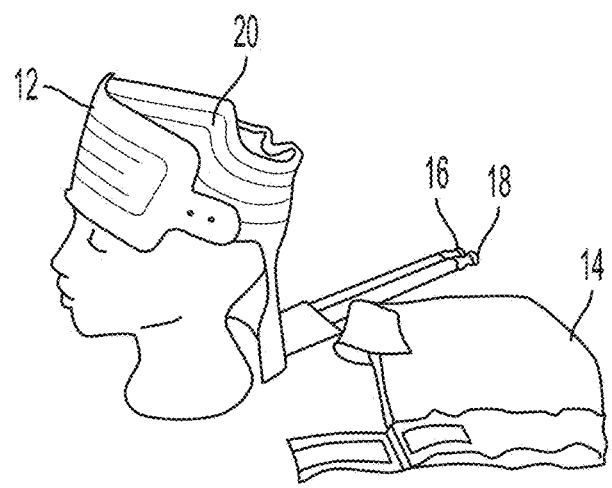
FIG. 2 depicts the cold cap assembly of FIG. 1, wherein the compression hood has been removed, and the circulating pad remains on the head.
Figure 5:
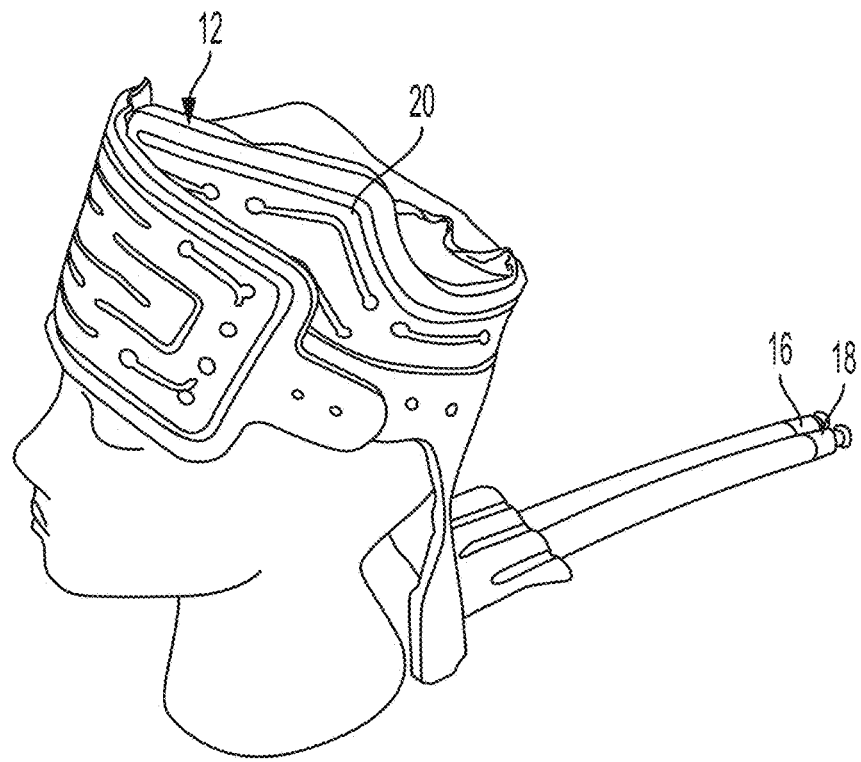
FIG. 5 is an enlarged view of the circulating pad of FIGS. 1 and 2, depicting the laminated structure thereof.

Scalp cooling may be provided using a cold cap assembly configured to be placed on a patient's head. The cold cap assembly is configured to extend in surrounding relationship to the patient's scalp, and includes one or more fluid channels through which a chilled fluid (e.g., water) is circulated. The one or more fluid channels are arranged such that chilled fluid circulated therethrough will cool the patient's scalp. In the embodiment shown in FIGS. 1-2 and 5, the cold cap assembly (10) includes a fluid circulating pad (12) configured to be wrapped around a patient's head, as shown. Circulating pad (12) includes one or more fluid channels (20) formed therein, as well as a fluid inlet (16) and a fluid outlet (18). The fluid inlet and outlet (16, 18) are in fluid communication with the one or more fluid channels (20) such that chilled fluid may be urged into inlet (16), circulated through the one or more fluid channels (20), and thereafter expelled through outlet (18). In the example shown, fluid conduits extend between inlet and outlet (16, 18) and fluid channels (20) of circulating pad (12).

Figure 6:
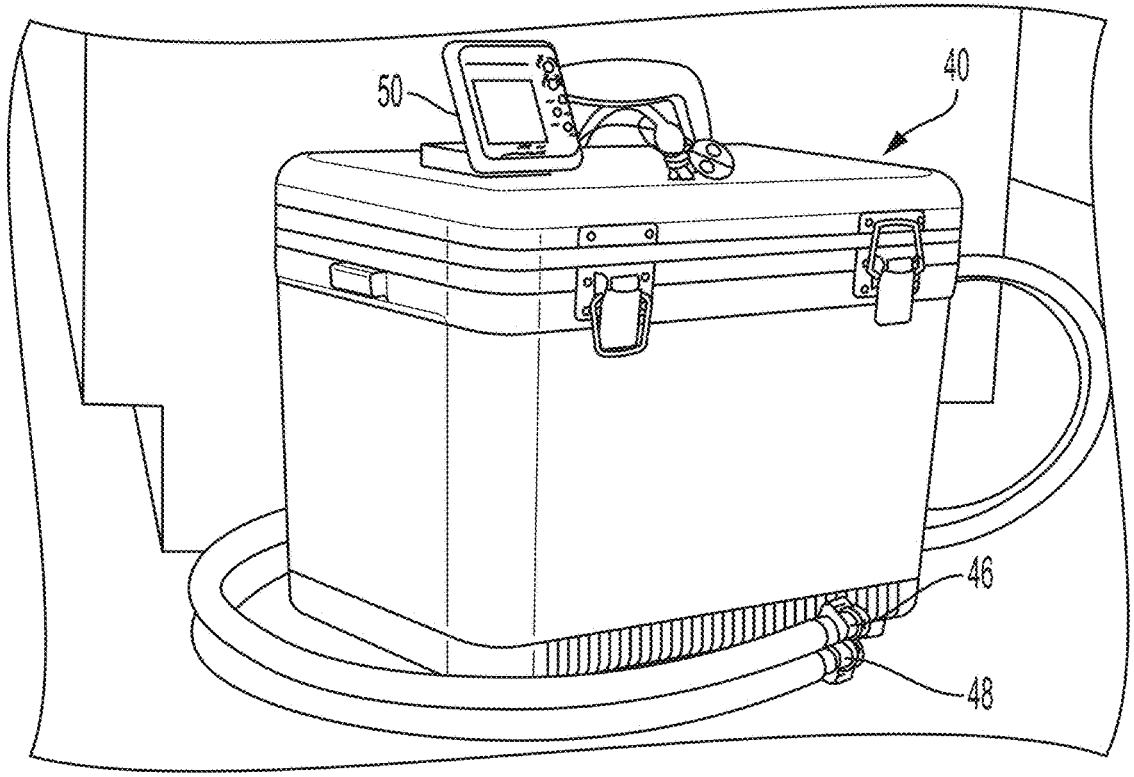
FIG. 6 is an embodiment of a portable cooling unit for use with the cold cap assembly.

Fluid inlet and outlet (16, 18) may be configured for attachment to corresponding fluid inlets and outlets on a fluid chiller unit. One such portable chiller unit (40) is depicted in FIG. 6. A portable chiller unit is also described in U.S. Pat. No. 7,640,764 (which is incorporated herein by reference). Other chiller units are shown and described in U.S. Patent Pub. Nos. 2011/0077723 A1, published Mar. 31, 2011, and 2009/0069731 A1, published Mar. 12, 2009, both of which are also incorporated herein by reference.

Chiller unit (40) in FIG. 6 includes fluid outlet (48) which may be detachably connected to fluid inlet (16) of circulating pad (12), and fluid inlet (46) which may be detachably connected to fluid outlet (18) of circulating pad (12). Any of a variety of connector elements may be employed. Chiller unit (40) is configured to expel chilled fluid from outlet (48), and then receive fluid returning from an attached circulating pad via inlet (46).

By providing a cold cap that can connect and disconnect to a small, portable chiller unit, applicant has discovered that follicle damage can be minimized. Furthermore, the additional capability of disconnecting the cold cap from one chiller unit and connecting to another portable chiller allows the patient to continue (and/or begin) hypothermy outside of the chemotherapy clinical environment, including the time moving to another department, traveling home, and while at home. For example, during a chemotherapy treatment session in a hospital, clinic or other medical facility, the cold cap worn by a patient may be operatively connected to a first chiller unit within the facility (which may or may not be a portable chiller unit such as shown in FIG. 6).

Once the chemotherapy session is completed, the cold cap may be disconnected from the first chiller unit. Thereafter, the cold cap, which remains on the patient's head, is then operatively connected to a second chiller unit (e.g., a portable chiller unit (40). The second chiller unit will pump chilled fluid through the cold cap as, for example, the patient is moved to another room (e.g., a post-treatment observation room within the same facility), or the patient returns home from the treatment facility.

By providing an easily transportable chiller unit, hypothermy can continue for a period of time after the chemotherapy drug(s) have been administered to the patient (e.g., while the patient returns home or is moved to a post-treatment room in the facility). This ability to continue hypothermy while in transit allows sufficient time for the metabolization of the cytotoxic products in the bloodstream while continuing to protect hair follicles from the toxic effects of those products (via scalp cooling). The portable chiller unit also permits hypothermy during home chemotherapy treatment. By way of example, a chiller unit below 10 kg, or even below 5 kg in weight, allows patients and caregivers to control and monitor cooling while the patient is in transit to and from therapy. A handle may be provided on the chiller unit to facilitate transport, as shown in FIG. 6. It should also be pointed out that, instead of using a separate chiller unit during actual administration of the chemotherapy, the same portable chiller unit may be used throughout the chemotherapy treatment session and for periods of time thereafter (e.g., while the patient travels to another room, facility or home).

This ability to control the duration and temperature of hypothermy independent of chemotherapy allows for better implementation of photo-stimulation of follicles. In addition, the schedule of hypothermy can be tailored to better cooperate with scheduled photo-stimulation.

Portable cooling unit (40) is configured to pump chilled fluid, at a controlled temperature, through an attached cold cap. Thus, cooling unit (40) includes a fluid reservoir for holding the circulating fluid, a temperature sensor, a control system for regulating the temperature (and optionally other parameters, such as fluid flow rate, duration of cooling, temperature schedule, etc.) of the circulated fluid, and a pump for expelling fluid into an operatively attached cold cap. As used herein, the term "circulating fluid" refers to the chilled fluid (e.g., water) which is circulated through the one or more fluid channels of an attached cold cap. The circulating fluid may be chilled in any of a variety of ways known in the art.

By way of example, circulating fluid delivered to the cold cap may be circulated through a heat exchanger in functional contact with a chilled thermal mass in order to cool the circulating fluid (i.e., by transferring heat from the circulating fluid to the chilled thermal mass). By way of example, portable cooling unit (40) may comprise an insulated device containing a chilled thermal mass. The mass can be any liquid, gas, or solid, such as a mass which is cooled to below 0 degrees Celsius. Potential materials include dry ice, liquid nitrogen, non-polar solvents, and polar solvents. In one embodiment, a water based mass is used, either pure or mixed with another substance to adjust the freezing point. Alternatively, a water mass may be cooled below freezing in order to permit the phase change of water changing from solid to liquid to absorb significantly more thermal energy from the circulating fluid than liquid water alone. As yet another alternative, one or more substances may be added to the water which lower the freezing point, thus allowing greater heat transfer than would be provided by water alone. The chilled thermal mass may be cooled internally within the cooling unit (40) (e.g., by vapor compression), or a chilled thermal mass (e.g., dry ice) may be added to an internal reservoir which is in thermal communication with the circulating fluid (i.e., via a heat exchanger). A chilled thermal mass (e.g., dry ice or ice) may be placed directly into the circulating fluid reservoir, and scalp cooling (i.e., scalp temperature) controlled merely by regulating the flow rate through the pad. A circulating pump for pumping the circulating fluid may be thermally isolated from the chilled thermal mass, venting waste heat away from the unit and minimizing the amount of heat transferred to the chilled thermal mass and the circulating fluid.

One or more temperature sensors, mixing devices and other control schemes or devices permit the amount of thermal transfer, and thus the circulating fluid temperature, to be accurately controlled. For example, one or more temperature sensors may be included in or on the circulating pad, such as in a location which ensures that the sensor will contact the patient's scalp and provide an accurate temperature signal to a control unit provided on the cooling unit, and/or a temperature display (50) shown in FIG. 6. In this manner, the temperature of the skin may be slowly reduced, such as to a temperature of about 37-38 degrees Fahrenheit. If the temperature is too low, tissue damage or other injury may result. If the temperature is too high, reduced efficacy may result.

The chiller unit may also be configured to provide precise temperature control as well as the duration of scalp cooling. For example, a control unit may be provided to not only monitor the temperature of the fluid being circulated through the cold cap, but also provide a predetermined (or user-determined) cooling regime. For example, the fluid temperature may be gradually lowered from an ambient temperature to the desired circulating fluid temperature over a period of time (e.g., 30 minutes). The control unit may include a user interface, such as a display screen, input device, etc. Scalp temperature may be regulated by controlling the temperature of the circulating fluid and/or controlling the flow rate of the circulating fluid through the pad.

The cold cap is configured to conform to the scalp. In the example shown in FIGS. 1-2 and 5, the cold cap is composed of two parts: a lightweight circulating pad weighing, for example, less than 290 grams, and constructed of laminated layers; and an outer compression hood or cap which provides compressive force so as to urge the circulating pad against the patient's scalp. Edges and internal tubes of the circulating pad may be constructed, for example, by welding or adhesively connecting various layers to one another. Weight may be minimized to prevent headaches and muscle strain. The outer lightweight waterproof compression cap presses the inner circulating pad against the scalp, causing it to conform to the scalp. The inner circulating pad may include one or more attachment points for one or more temperature sensors. These sensors relay the temperature of the scalp to an external display (50) and/or the control system which regulates fluid temperature and/or the circulating pump.

The circulating pad generally comprises a heat transfer member, and therefore at least a portion of the pad may be fabricated from a thermally conductive material and configured to cover at least a portion of the hair follicles of a wearer. A pliable member such as a foam or similar material may be provided on the skin-contacting surface of the circulating pad. While the depicted examples show a cold cap for use on the head, the cold cap may alternatively be configured for use on a wearer's face, pubic region or other part of the body where it is desired to limit hair loss. Fluid may be circulated through the pad at a temperature of, for example, 0 to 20 degrees C.

The cold cap can be decoupled from the portable unit and attached to a larger unit (with higher cooling capacity) without removing or adjusting the cap on the patient's head. The cold cap may be constructed to be able to adjust and be customized to fit individual patients so that it can be used multiple times comfortably.

Power for sensing, controls and circulation may be provided by external power sources, including but not limited to, wall socket power and car cigarette lighter power. The unit contains electrical inputs permitting the unit to be attached to either power source. In an alternate embodiment, the cooling unit includes a battery to permit continuous use when external power is not practical.

In some embodiments, the cooling unit is portable. The patient or caregiver can manually carry the cooling unit to and from chemotherapy and/or to and from home or hospital room.

The cooling unit may also include a timer function that can control a time-temperature profile for the patient. The profile can be customized for the patient and type of chemotherapy. In addition, it can be programmed to discontinue cooling after a preset period of time in preparation for phototherapy.

Controls, circuitry, inputs, and outputs of the hypothermy system are generally electronic (analog or digital).

Figure 3:
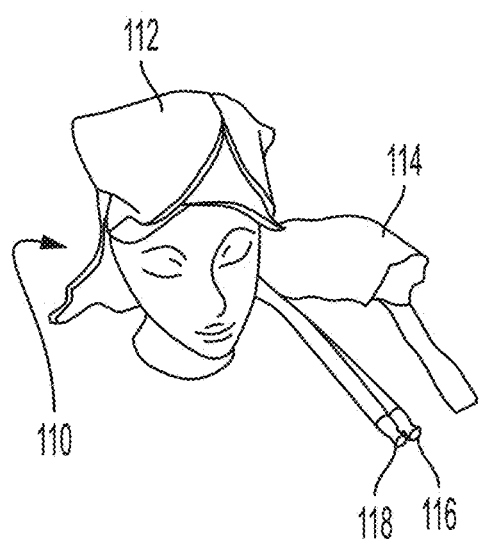
FIG. 3 depicts an alternative embodiment of a cold cap assembly, wherein the compression hood has been removed from the head.
Figure 4:
FIG. 4 depicts the embodiment of FIG. 3, fully fitted on a head.

FIGS. 3 and 4 depict an alternative embodiment of a cold cap (110) having a circulation pad (112), a compression hood (114) and a fluid inlet and outlet (116, 118).

The following illustrates some additional features of the cold cap, which may or may not be included in various embodiments thereof. Therefore, these exemplary features are not intended to be limiting in any way.

Cold Cap Attributes:
Lightweight headpiece
Individualized liquid pathways for Left and Right halves
Liquid entry and exit on each side
Located on back of the neck
Thin pathways (⅛") with faster fluid flow—allowing for low cap-weight maintenance
Each side pathways allows for zigzag pattern for liquid to travel and cool down the scalp
Foam-based Air cushion between the chamber and scalp to prevent frostbite
Washable foam piece and cap
Temperature sensors at ingress and egress
Tubes length of 6' to allow for flexibility to move the refrigeration unit around, but not get the tubes tangled
Ingress and egress tubes marked and connectors of different shape to prevent cross-connection
One-way valves at each connection to prevent liquid dripping
Multicolor for ladies and gents
Refrigeration unit:
Weighs less than 10 lbs
Wall plug and car-lighter-adapter to power condenser and liquid flow
Easy to grip and carry handle
Uses common distilled water as the circulating fluid
Electronic digital readers for Temperature (ingress, egress), countdown to optimal water temperature, timer to track length of time
Electronic timer to shut off system after desired time
Default 30-minute timer with rocker-buttons to increase/decrease time in 10-minute increments
Start and Stop buttons
Gradual cooling over controlled period of time to allow patients to adjust to cooler temperature
Hi-grade water pump
Seal-able water reservoir with insulation to prevent condensation buildup
Red/Green tab to reflect the reservoir is closed
Ability to bleed out air at initial start-up; ability to introduce air into circulation at end of cooling cycle As mentioned previously, the cold cap is used during administration of chemotherapy drugs and for a period of time thereafter in order to limit the ability of the drugs to damage the patient's hair follicles. However, applicant has discovered that scalp cooling alone cannot completely prevent chemotherapy-induced hair loss. However, by combining scalp cooling with photo-stimulation of hair follicles, unexpectedly improved results are obtained. Photo-stimulation scalp therapy promotes hair regrowth in follicles damaged by the chemotherapy.

Figure 7:
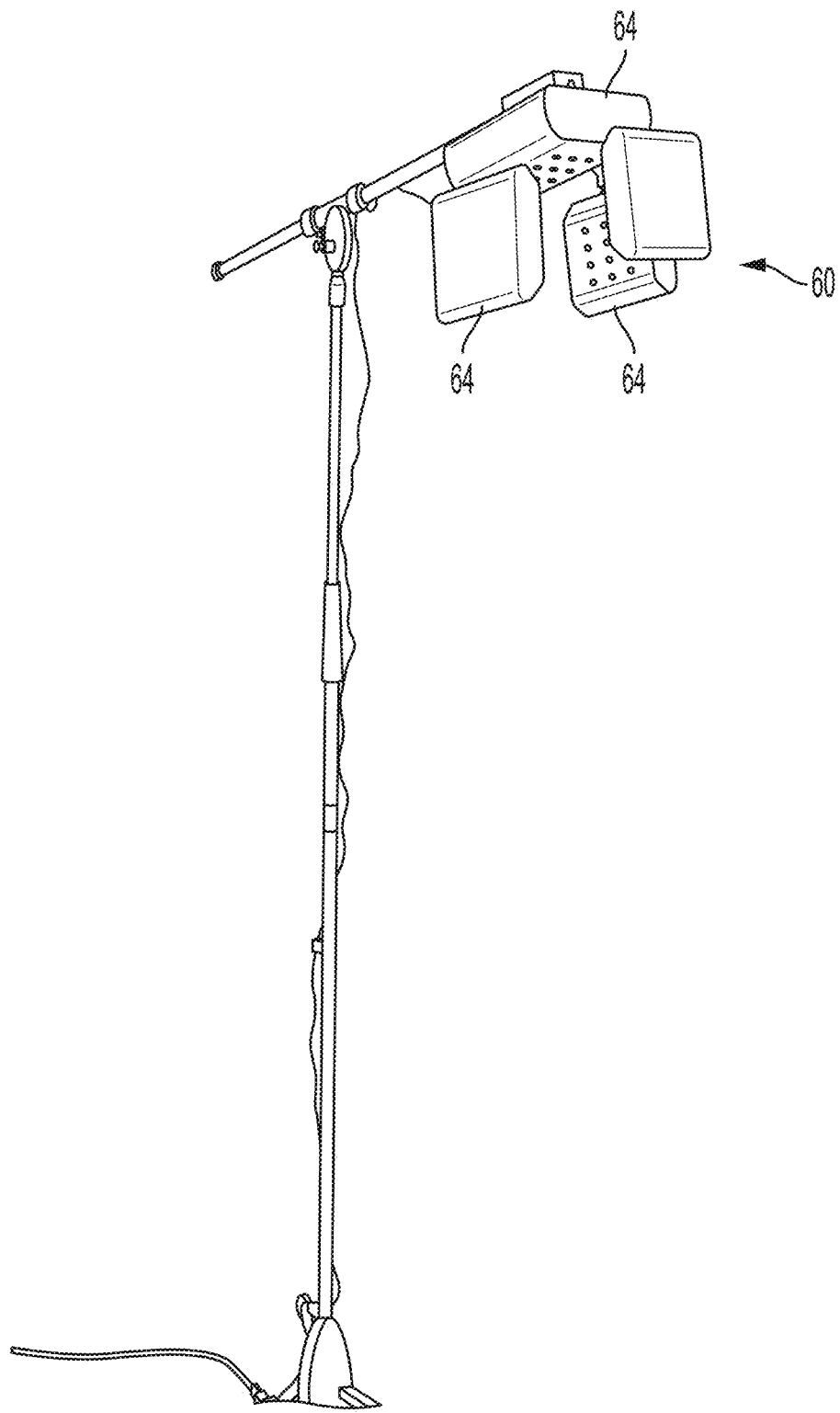
FIG. 7 is an embodiment of a laser treatment unit.
Figure 8:
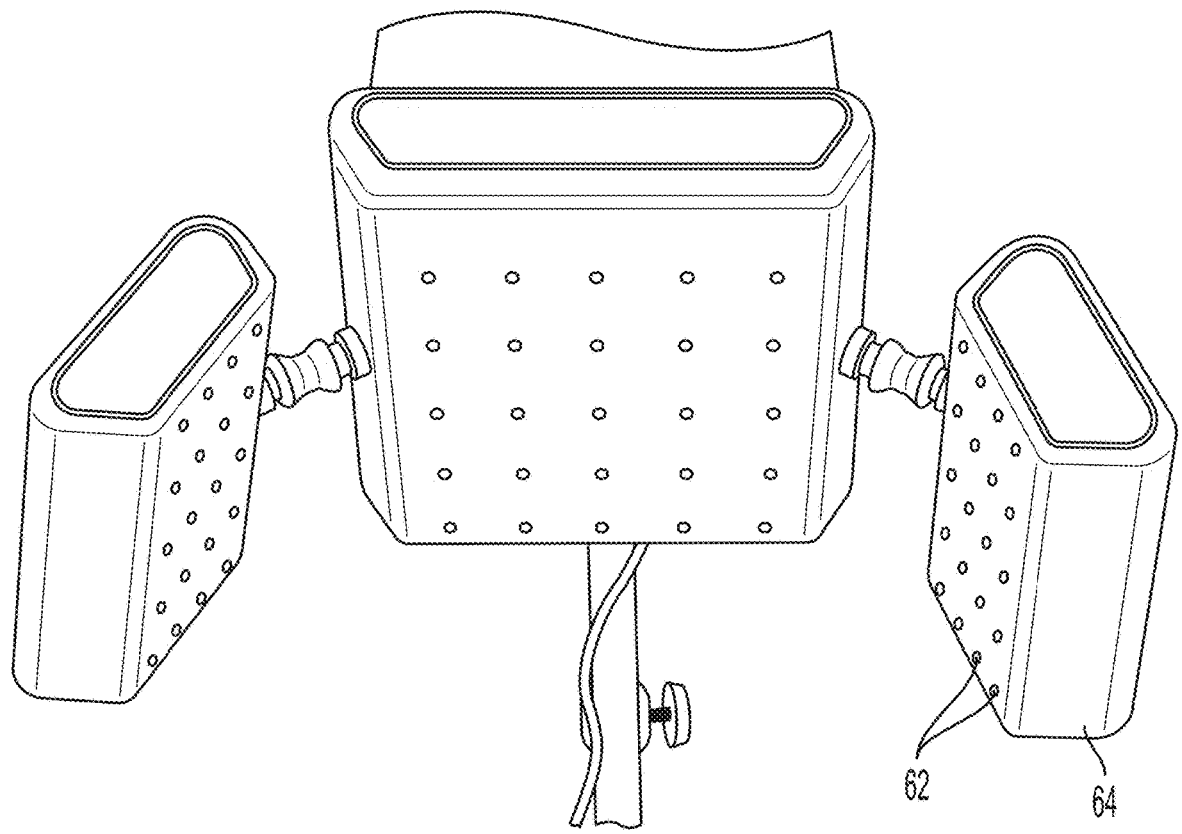
FIG. 8 is a close-up view of part of the treatment portion of a laser treatment unit, depicting multiple light sources.
Figure 9:
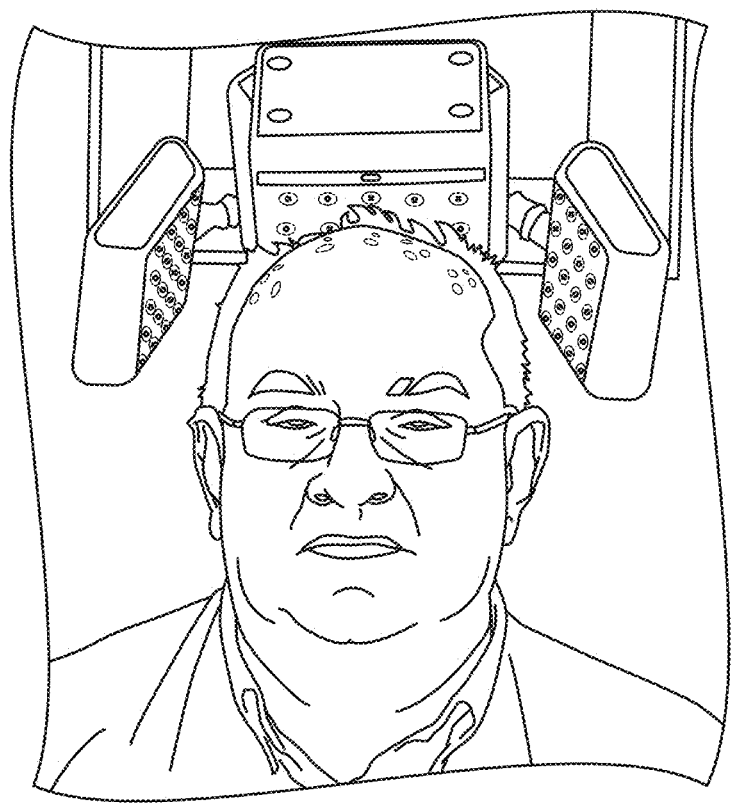
FIG. 9 depicts the laser treatment unit in use.

The photo-stimulation scalp therapy system generally includes at least one source of light configured to apply emitted light to the patient's scalp. A plurality of light sources such as light emitting diodes, laser emitters, or other devices may be used, such as those emitting light around 640-660 nm. In one example, laser diodes are used. FIGS. 7-9 depict an exemplary laser scalp treatment system (60) which employs a plurality of laser emitters (62) for providing low-level laser therapy which promotes hair regrowth in damaged follicles. By way of example, the laser emitters may comprise individual semiconductor devices, such as laser diodes. In the embodiment shown, the laser diodes are provided on four adjustable panels (64) mounted on a support stand. The panels (64) may be adjusted for arrangement around a patient's head, in close proximity thereto (e.g., 1 to 2 inches from the scalp, see FIG. 9). Any of a variety of laser diodes may be used, such as those emitting at 600-700 nm, 620-680 nm, or 640-660 nm. In the example shown, the laser diodes are 650 nm, 5 mW devices.

The following illustrates some additional features of the laser system, which may or may not be included in various embodiments thereof. Therefore, these exemplary features are not intended to be limiting in any way.

Hair-Rejuvenation Laser System
- 4-panel system to cover top (4"×6"), sides (3"×5") and back (3"×5") of head
- Free-standing equipment using elongated neck and tripod peds at least foot from the ground
- Extender arm to support the 4-panel system
- Each panel with individual lasers at 1" apart with ½" gap from sides
- Top panel has 25 laser diodes, and each of the three side panels have 20 laser diodes
- Each panel with independent adjustment ability to contour to patient's head
- Electronic panel with On, Off, Timer countdown, addition/subtraction of minutes in 10-minute increment
- Default 30-minutes during session initiation The laser system may include a control system which regulated the amount of time which the unit may be used. For example, the system may be configured such that laser scalp therapy may be applied to a patient for no more than 20 minutes, 30 minutes, or some other predetermined period of time in order to prevent patient injury or overuse. The control system may also be configured such that the unit may not be turned back on for a predetermined period of time following use.

Figure 10:
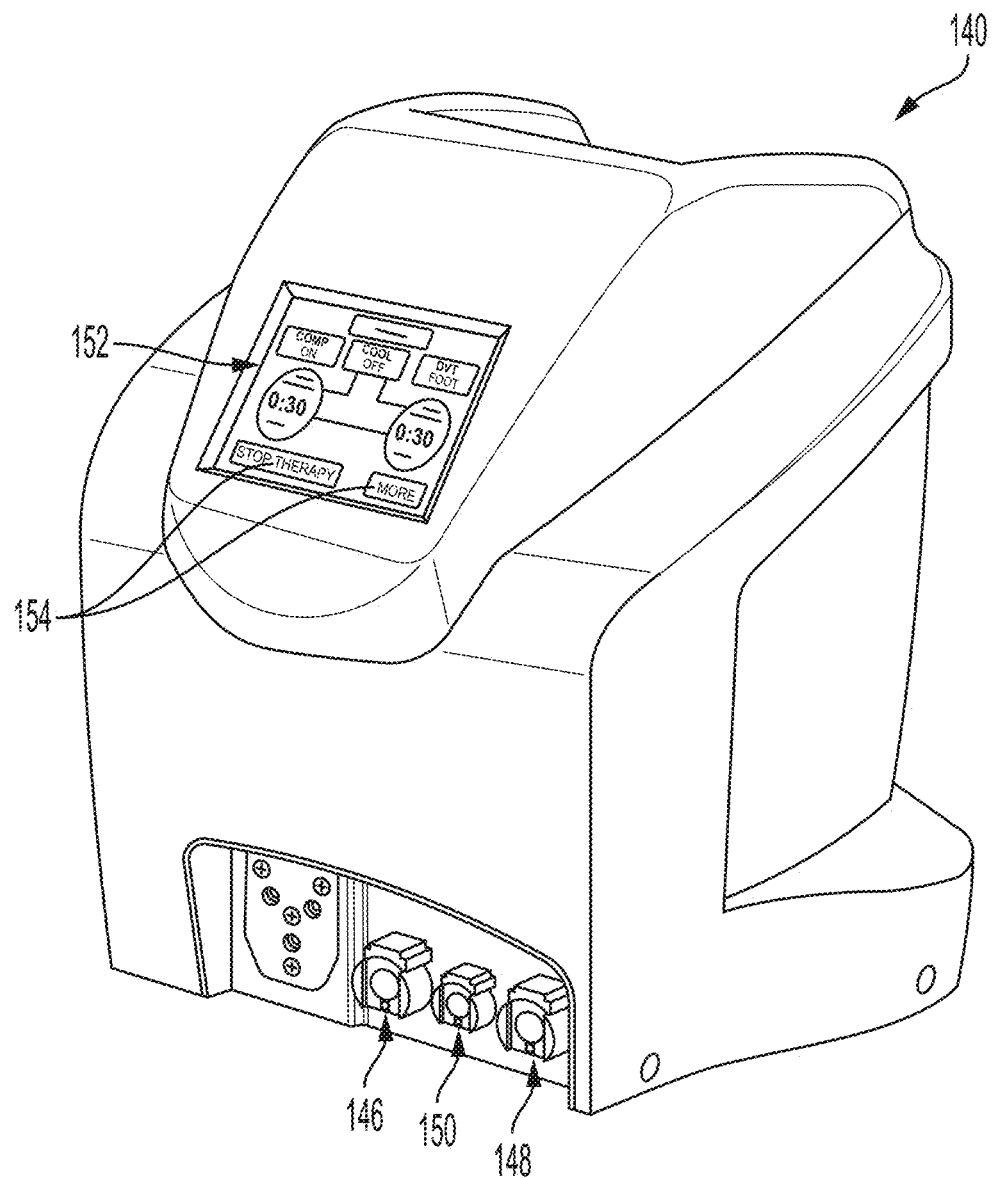
FIG. 10 depicts an alternative embodiment of a portable cooling unit for use with the cold cap assembly of FIGS. 11-13, wherein the cooling unit also provides compression.
Figure 12:
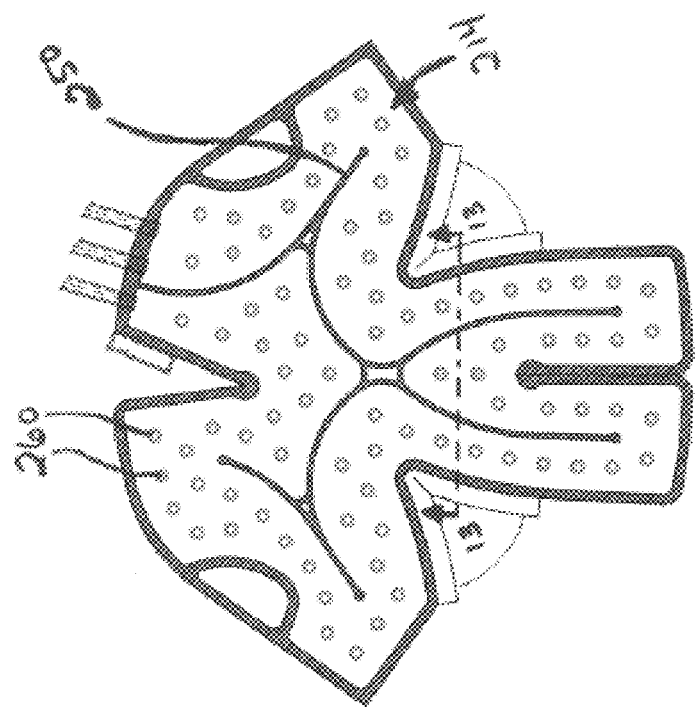
FIG. 12 is a top schematic view of the inner layer of the cold cap assembly of FIG. 11.

One exemplary, non-limiting process for preventing hair loss and promoting hair-rejuvenation is as follows:
- The process requested for patent provides hair-loss-prevention therapy to the cancer patient during chemotherapy and hair-growth-therapy post-chemotherapy treatment process.
- Hair-loss-prevention therapy encompasses Cold Cap and Refrigeration system that is applied 30 minutes prior to each chemotherapy session and for 120-180 minutes after each session for the whole duration of the chemotherapy treatment of cancer. The scalp may be cooled from normal temperature to the target (e.g., 37-38 F) over a period of time, such as gradual scalp cooling over a period of 30 minutes.
- Following scalp cooling, the laser system is used to promote hair rejuvenation. This is done not only every day following chemotherapy, but also once per day thereafter even if chemotherapy is not being provided on that day.
- Once the chemotherapy treatment round has been completed, the patient then uses the Hair-rejuvenation Laser system daily to stimulate hair follicle regeneration. This therapy would continue for 9-months to 12-months or longer, based on desired outcome by the patient FIG. 10 depicts an alternative embodiment of a portable chiller unit (140) which also provides compression when operatively connected to a suitable cold cap. Fluid outlet (146) and inlet (148) configured for detachable attachment to corresponding fluid inlet and outlet conduits (e.g., hoses) associated with a cold cap. Outlet (148) and inlet (146) are depicted as including quick connects which facilitate attachment and detachment to the fluid conduits of the cold cap. A third outlet (150) is also provided on chiller unit (140), and the unit (140) is configured to deliver pressurized fluid (e.g., air) through outlet (150) for purposes of providing scalp compression. Chiller unit (140) is configured to expel chilled fluid from outlet (148), and receive fluid returning from an attached circulating pad (e.g., the cold cap) via inlet (146).

A return for pressurized air is not required, since unit (140) controls scalp compression simply by regulating air pressure within an air chamber of the cold cap. For example, chiller/compression unit (140) may include an air pump (e.g., as described in US 2009/0069731) which is in communication with outlet (150) for controllably expelling air therefrom into an air chamber of the cold cap. Unit (140) may also include a vent valve or other structure for controllably releasing air from the cold cap through outlet (150) (i.e., air flows out of and into outlet (150) in order to control air pressure within the cold cap). By way of example, unit (150) may be configured to supply air at a controlled pressure of about 15 mm Hg, 10 mm Hg, or other desired pressure(s).

Portable cooling unit (140) is also configured to pump chilled fluid, at a controlled temperature, through an attached cold cap. Thus, cooling unit (140) includes a fluid reservoir for holding the circulating fluid, one or more temperature sensors, and a pump for expelling fluid into an operatively attached cold cap. Cooling unit (140) also includes a control system for regulating fluid temperature, fluid flow rate, air pressure, duration of scalp cooling, duration of scalp compression, and optionally other parameters of the circulated fluid and pressurized air. The control system generally includes one or more processors (e.g., a CPU) capable of processing instructions stored in a memory for controlling the operation of unit (140). The circulating fluid may be chilled in any of a variety of ways known in the art, as discussed above.

One or more temperature sensors, mixing devices and other control schemes or devices permit the amount of thermal transfer, and thus the circulating fluid temperature, to be accurately controlled. For example, one or more temperature sensors may be included in or on the cool cap, such as in a location which ensures that the sensor will contact the patient's scalp and provide an accurate temperature signal to a control unit provided on the cooling unit, and/or a display screen (152) shown in FIG. 10.

The chiller unit (140) may also be configured to provide precise temperature control as well as the duration of scalp cooling. For example, the control system therein not only monitors the temperature of the fluid being circulated through the cold cap, but also provides a predetermined (or user-determined) cooling regime. For example, the fluid temperature may be gradually lowered from an ambient temperature to the desired circulating fluid temperature over a period of time (e.g., 30 minutes) prior to administration of the chemotherapeutic agent(s). The unit (140) includes a user interface comprising display screen (152) and a plurality of input devices (154), such as touch sensitive areas on display screen (152), one or more input keys, or various other types of input devices known to those skilled in the art. Scalp temperature may be regulated by controlling the temperature of the circulating fluid and/or controlling the flow rate of the circulating fluid through the pad.

Chiller/compression unit (140) may also include an interface (e.g., a USB port) which allows the input of patient data (e.g., patient name and/or other identifier, patient information such as weight, chemotherapeutic agent(s) to be administered, chemo. agent(s) dosage, duration of administration of chemo. agent(s), etc.) via electronic transfer. For example, unit (140) will load a patient file into memory from a memory device (e.g., a portable USB memory device) attached to the interface. Of course it is also contemplated that the patient data may be input via input devices (154), by communication with a data store (e.g., wirelessly) or other ways known to those skilled in the art. The control system of unit (140) may be configured (e.g., programmed) to use the inputted data to control the operation of scalp cooling and scalp compression. By way of example, based on the identity of the chemo. agent(s) and dosage(s), and optionally patient weight, duration of chemo. administration, etc., the control system may look up the half-life of the chemo. agent(s) to be delivered (from information stored in memory) and calculate the appropriate duration of scalp cooling (e.g., to ensure scalp cooling continues until the agent(s) have lost at least 50%, or even 75% (or 90%) of its activity. The display screen will then display instructions to the user, such as displaying when to activate cooling (e.g., a button to start therapy) prior to chemo. infusion, indicating (audibly and/or visually) when the scalp has been sufficiently cooled so that infusion should begin, and indicating (audibly and/or visually) when scalp cooling has ended (e.g., when the activity of the chemo. agent(s) is expected to have been reduced by 50% or more). A library of data for various chemo. agent(s) is stored in memory for use by the control system for these purposes. Of course a medical practitioner, or in some cases a patient, may also control operation of unit (140) using input devices (154) and/or providing desired cooling and compression parameters for a patient.

FIGS. 11-14 depict an alternative embodiment of a cold cap (210) configured to conform to the scalp. The cold cap assembly (210) is configured to extend in surrounding relationship to the patient's scalp, but is shown in unassembled form in FIGS. 11 and 12. Cold cap (210) is formed from three layers of material (e.g., fluid impermeable plastic) (212, 214, 216) which are sealingly attached around their periphery so as to form a cooling fluid chamber (230) and an air chamber (232) (see FIG. 13). Cooled fluid is delivered into fluid chamber (230) though an inlet conduit (or tube) (240), traverses through the cooling fluid chamber (230) and exits through the outlet conduit (or tube) (242). Inlet and outlet conduits (240, 242) are configured for detachable attachment to the fluid outlet and fluid inlet of the chiller unit (40, 140).

Figure 11:
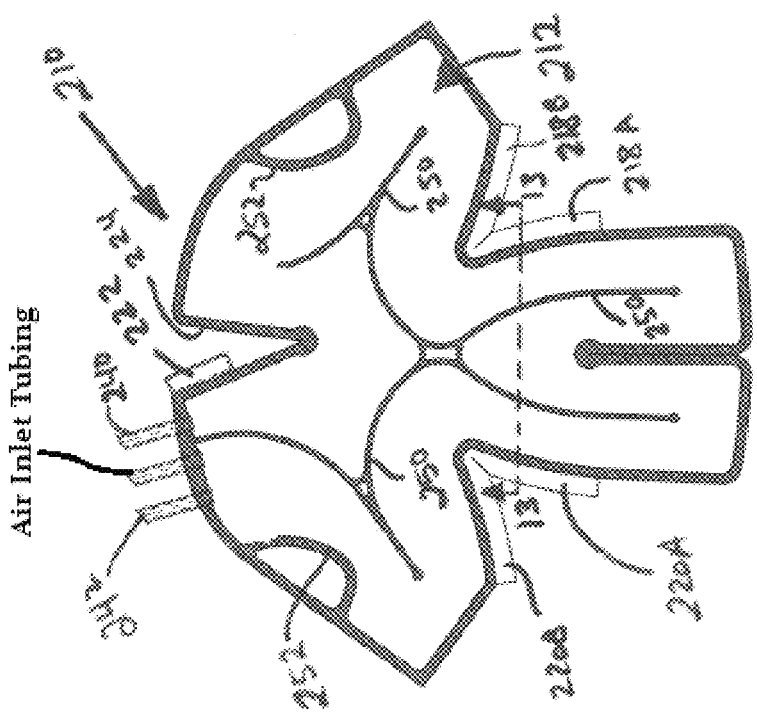
FIG. 11 is a top schematic view of an alternative embodiment of a cold cap assembly.

To assemble the cold cap from the structure shown in FIG. 11 so as to provide a cold cap similar in appearance to that shown in FIG. 4, adjacent edges are joined together (e.g., by heat sealing) such that tab (218A) is sealed to tab (218B), and tab (220A) is sealed to tab (220B) so as to form a skull conforming cap. A hook and loop fastener combination (222, 224) is also provided so that the diameter of the cold cap may be adjusted for proper fit.

Figure 13:
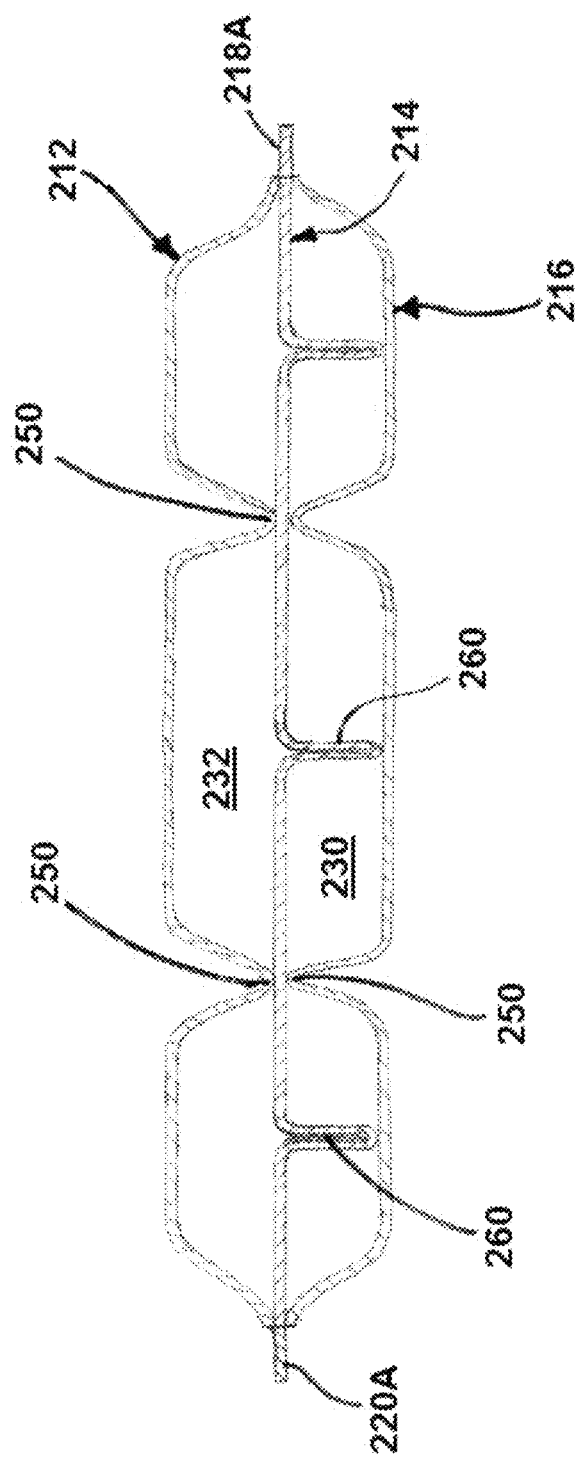
FIG. 13 is a schematic cross-sectional view of the cold cap assembly of FIGS. 11 and 12, taken along the line 13-13 in FIGS. 11 and 12.

The three layers of material (212, 214, 216) are joined to one another about their peripheries such as by heat sealing. As seen in FIG. 13, this provides fluid cooling chamber (230) between second and third layers (214, 216), and air chamber (232) between first and second layers (212, 214). In order to provide additional support, as well as define a serpentine or other suitable flow pattern within fluid cooling chamber (230), the three layers are sealed to one another along internal seam (250) such as by heat sealing. In this manner, fluid cooling chamber (230) defines a flow pattern by which the chilled fluid (e.g., water) will circulate over and about the patient's head so as to provide generally uniform cooling of the scalp. It should also be noted that a second set of internal seals (252) is also provided on each side of the cold cap in the area of the patient's ears. This prevents cooling from being applied to the patient's ears during use.

In order to provide further support, a plurality of columnar seals (260) are also provided between second and third layers (214, 216) such as by heat sealing the two layers at a plurality of points. These columnar seals (260) act as support columns, and also act to break up water flow through fluid cooling chamber (230) which improves heat transfer (i.e., cooling of the scalp).

Figure 14:
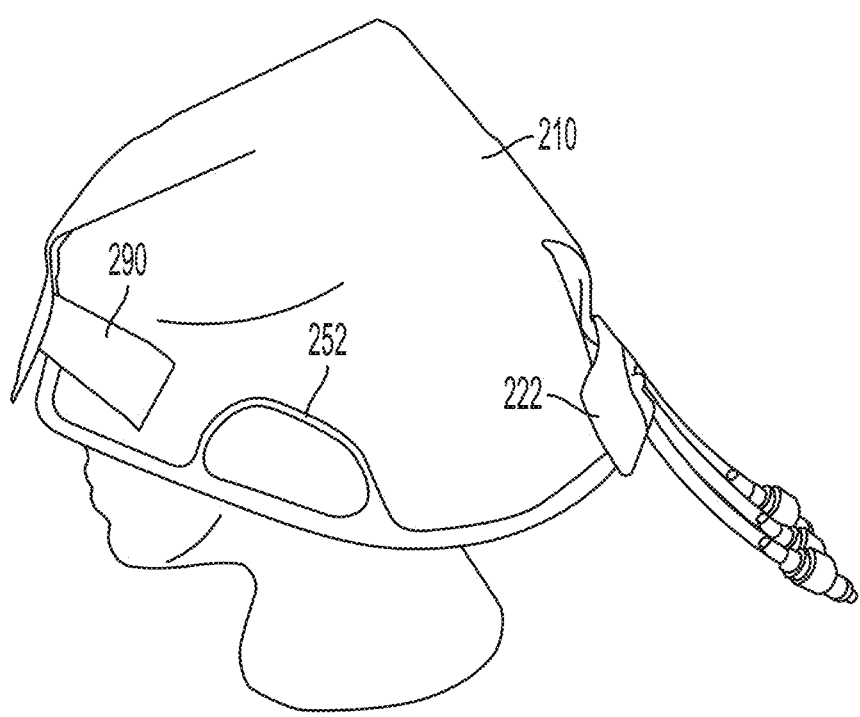
FIG. 14 depicts the cold cap assembly of FIGS. 11 and 12, in assembled form on a head.

FIG. 14 depicts cold cap assembly (210) in assembled form position on a head. It should be noted that cold cap assembly (210) in FIG. 14 includes an additional hook and loop fastener (290) across the forehead region, and a similar additional hook and loop fastener (290) is provided on the other side of the forehead (but is not visible in FIG. 14).

In some embodiments of the methods described herein, a wetting agent composition is applied to the patient's hair in order to improve thermal conductivity and hence scalp cooling. The wetting agent composition generally comprises a humectant such as glycerin, although other pharmaceutically acceptable humectants may be employed. The wetting agent composition may also comprise water, fragrance, and additives having antibacterial properties. One exemplary composition comprises about 50-95% glycerin by weight, with the balance being water. Fragrance and other additives may be added to this composition, as desired. One particular composition comprises about 86% glycerin, about 8% water, and about 5% fragrance.

While several devices and components thereof have been discussed in detail above, it should be understood that the components, features, configurations, and methods of using the devices discussed are not limited to the contexts provided above. In particular, components, features, configurations, and methods of use described in the context of one of the devices may be incorporated into any of the other devices. Furthermore, not limited to the further description provided below, additional and alternative suitable components, features, configurations, and methods of using the devices, as well as various ways in which the teachings herein may be combined and interchanged, will be apparent to those of ordinary skill in the art in view of the teachings herein.

Versions of the devices described above may be actuated mechanically or electromechanically (e.g., using one or more electrical motors, solenoids, etc.). However, other actuation modes may be suitable as well including but not limited to pneumatic and/or hydraulic actuation, etc. Various suitable ways in which such alternative forms of actuation may be provided in a device as described above will be apparent to those of ordinary skill in the art in view of the teachings herein. Versions of the devices described above may have various types of construction.

Having shown and described various versions in the present disclosure, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometries, materials, dimensions, ratios, steps, and the like discussed above are illustrative and are not required. Accordingly, the scope of the present invention should is understood not to be limited to the details of structure and operation shown and described in the specification and drawings.

What is claimed is:

1. A cold cap for use in limiting chemotherapy-induced hair loss in a patient, said cap adapted for connecting to a chiller unit for circulating chilled fluid through the cap and receiving pressurized air for supplying compression to the scalp of a patient, wherein said cap comprises:

at least three layers of fluid impermeable material which are sealingly attached around their periphery so as to form a cooling fluid chamber configured to cool the scalp when chilled fluid is circulated through the cooling fluid chamber, and an air chamber configured to apply compression to the scalp when pressurized air is supplied to the air chamber;

fluid inlet and outlet conduits in fluid communication with said cooling fluid chamber and configured for detachable attachment to a fluid outlet and a fluid inlet of the chiller unit;

air inlet tubing in communication with said air chamber;

a first internal seal that seals said at least three layers to one another, said first internal seal spaced inwardly of the sealed periphery of said at least three layers so as to provide additional support and define a serpentine flow pattern within said cooling fluid chamber, thereby defining a flow pattern by which chilled fluid can be circulated over and about the patient's head so as to provide generally uniform cooling of the patient's scalp; and second and third internal seals located along opposite sides of said cap, said second and third internal seals extending inwardly from the sealed periphery of said at least three layers, such that each of said second and third internal seals together with an adjacent portion of said sealed periphery define regions within said cap that are not in fluid communication with said cooling fluid chamber;

wherein said cap is adapted to be worn by the patient such that the cap extends in surrounding relationship to and conforming to the patient's scalp, with said regions not in fluid communication with said cooling fluid chamber extending over the patient's ears such that cooling is not applied to the patient's ears during use.

2. The cold cap of claim 1, wherein said air chamber is located between a first layer and a second layer of said at least three layers, and said cooling fluid chamber is located between said second layer and a third layer of said at least three layers, and further comprising a plurality of columnar seals extending between and connecting said second and third layers, wherein said columnar seals act as support columns and break up water flow through said fluid cooling chamber.

* * * * *